United States Patent [19]  [11] 4,353,902
Hedde et al.  [45] Oct. 12, 1982

[54] LIVESTOCK FEED AND METHOD FOR IMPROVING FOOD UTILIZATION

[75] Inventors: Richard D. Hedde, West Chester; Roger C. Parish, King of Prussia, both of Pa.

[73] Assignee: SmithKline Corporation, Philadelphia, Pa.

[21] Appl. No.: 189,540

[22] Filed: Sep. 22, 1980

[51] Int. Cl.³ .............................................. A23K 1/16
[52] U.S. Cl. ................................... 424/250; 426/635; 426/636; 426/807; 426/2; 424/273 N; 424/270; 424/273 R; 424/285
[58] Field of Search ............... 426/2, 635, 636, 807; 424/273 N, 250, 270, 285

[56] References Cited

U.S. PATENT DOCUMENTS

| | | | |
|---|---|---|---|
| 2,438,353 | 3/1948 | Turner et al. | 426/2 |
| 3,808,336 | 4/1974 | Durant et al. | 424/273 |
| 3,950,333 | 4/1976 | Durant et al. | 424/273 |
| 3,950,353 | 4/1976 | Durant et al. | 260/309 |

OTHER PUBLICATIONS

Holroyde et al., Jour. Phar. & Exp. Ther., vol. 201(1) 1978, pp. 183–188.

Primary Examiner—Jeanette M. Hunter
Attorney, Agent, or Firm—William H. Edgerton; Richard D. Foggio; Alan D. Lourie

[57] ABSTRACT

Supplemented livestock feedstuffs and methods of feeding using as active ingredient a chemical compound having histamine $H_2$ antagonist activity improve the utilization of food by meat producing animals. A specific compound of use as the active ingredient is metiamide.

17 Claims, No Drawings

LIVESTOCK FEED AND METHOD FOR IMPROVING FOOD UTILIZATION

This invention comprises a novel animal feed composition, premixes for preparing said animal feed composition and a method for improving the food utilization and growth rate of meat producing animals using as an active ingredient one or more chemical compounds having histamine $H_2$-antagonist activity.

DESCRIPTION OF THE PRIOR ART

Compounds having histamine $H_2$ antagonist activity are a relatively new group of compounds which are useful in treating gastric and peptic ulcers in humans. Their activity is primarily due to an antagonistic effect at the histamine $H_2$ receptor centers which control acid secretion in the gastrointestinal tract. Usually, but not always, these compounds do not possess antagonistic activity against histamine $H_1$ receptors the end result of which is traditional antihistamine activity such as antiallergic activity.

In the last decade when these compounds with their new pharmacodynamic use were found many patents and scientific publications have become available to the public describing various chemical classes of compounds having $H_2$ antagonist activity. To date only one compound, cimetidine, U.S. Pat. No. 3,950,333, has been marketed to treat ulcers in humans due to its histamine $H_2$ antagonist activity. Earlier metiamide, U.S. Pat. No. 3,950,353, was studied in humans as an antiulcer agent for oral administration. While effective, metiamide was not developed further because of a low incidence of agranulocytosis. Even earlier burimamide, U.S. Pat. No. 3,808,336 was described to be active primarily after parenteral injection.

No compound having histamine $H_2$ antagonist activity has been described to be useful to enhance the food utilization of meat producing animals.

DESCRIPTION OF THE INVENTION

This invention comprises new feedstuffs for meat producing animals which have dispersed uniformly therein a quantity of one or more chemical compounds which have histamine $H_2$ antagonist activity said quantity being effective for increasing food utilization but not overtly toxic to the animals. It also comprises a method for improving the efficiency of food utilization and the growth rate of livestock per unit of feed. Such feedstuffs may comprise supplemented complete or basal animal feeds or, alternatively, premixes for preparing such feeds.

The carrier or basal feed is any used in the livestock industry usually hay or corn derived but may include dried fermentation residue, alfalfa, cottonseed, barley meal, soybean meal, corn meal, rice hulls, molasses, mineral salts, vitamins, silages, beet pulp, citrus pulp, fish meal, oats, rice bran, milo, sesame meal, milk or other standard animal feed ingredients. In general therefore the feedstuff carrier may be a partial or complete feed as well as a roughage composition.

Also included for commercial purposes are premix compositions in which the active ingredient is mixed in high concentration with a carrier ingredient which is usually desirable in the complete feed such as soybean meal, corn oil, ground corn, barley, mineral mixtures such as vermiculite or diatomaceous earth, corn gluten meal, corn distillers solubles or soyflour. Such premixes may often be marketed in 10–50 lb. bags and have in the present invention, a preferred concentration of about ½–3% by weight of active ingredient base. Preferably the premix carrier is grain or grain derived.

The active chemical ingredient of the animal feed composition described above may be any compound which has demonstrable histamine $H_2$ antagonist activity which results in improved food utilization at a feed level which is nontoxic or detrimental to the animal. Examples of the chemical compounds useful in this way are:

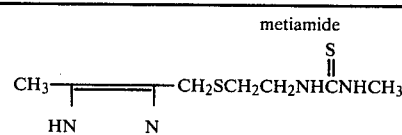

metiamide — U.S. Pat. No. 3,950,353

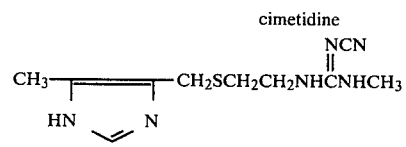

cimetidine — U.S. Pat. No. 3,950,333

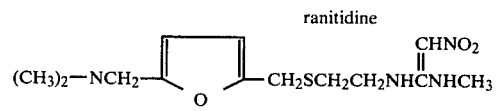

ranitidine — U.S. Pat. No. 4,128,658

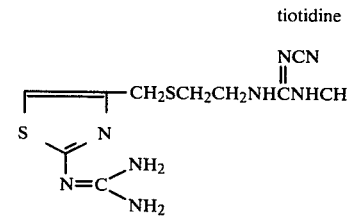

tiotidine — U.S. Pat. No. 4,165,378

-continued etintidine    U.S. Pat. No. 4,112,234

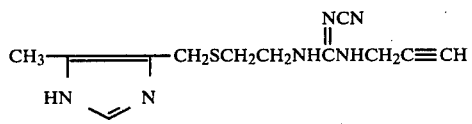

oxmetidine    U.S. Pat. No. 4,218,452

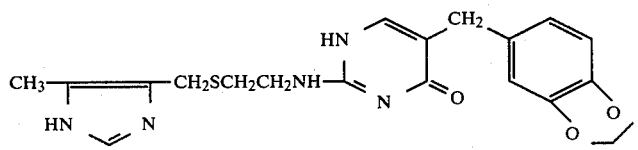

Any other chemical compound which possesses substantial histamine $H_2$ antagonist activity but no overt toxicity or other detrimental effects to the livestock is also useful as an active ingredient in this invention since it is believed that the increased feed utilization is due to the $H_2$ antagonist activity and not an artifactitious activity.

Among the references in the literature which disclose chemical compounds having histamine $H_2$ antagonist activity from which one skilled in the art can select candidates for being active ingredients in the animal feedstuffs and methods of this invention are: Belgian Pat. Nos. 857,388, 866,156, 866,155, 866,159, 867,105, 867,106, 875,846, 877,899, 867,594, 880,066, 879,024, 882,071; European Patent Application Nos. 1699, 2930, 3640, 6286, 6679, 11720; Japanese Patent and Application Nos. 103,468, 103,469, 5-4046-780, J5-3132-558, J5-3141-271, J5-5015-414, J5-4106-468; USSR Pat. No. 596,577; German Patent Application No. 2,805,824, 2,905,134; British Patent Application No. 80/06354; South African Patent Application No. 80/1151 and Script No. 467, page 12.

The fact that $H_2$ antagonists would enhance feed utilization is in itself surprising since, as is well known in the art, hydrochloric acid causes feed protein to denature as one of the first steps of digestion in many animal species.

The prime objective of this invention therefore comprises an animal feed composition as described above supplemented by a quantity of one or more chemical compounds which is effective for producing histamine $H_2$ antagonism but which is not toxic to the meat producing animal. The result is an improvement in food utilization and growth rate per unit of feed of the animal.

In a minor proportion of the meat producing animals, excessive secretion of hydrochloric acid causes physical damages in the stomach of monogastrics such as swine, proventriculus of poultry or abomasum of ruminants. This excess acid may cause ulcers in swine or gizzard erosion in broilers for example. Use of the supplemented feedstuffs and methods of this invention minimizes such effects, however, the increased food utilization resulting from this invention does not depend on the therapeutic activity since the food effect occurs in normal healthy animals as well.

Reduction of acidity in the intestinal tract such as in the abomasum and proximal small intestine of ruminants promotes a more favorable environment for starch utilization which is optimal at the range of about 6.5 to 7.5 pH.

Exemplary of the effective quantities of active ingredient are those selected from about 5–180 g per ton of feed of metiamide base. A preferred range from which selection may be made is from about 6–40 grams per ton.

The amounts of other chemical compounds having histamine $H_2$ antagonist activity in the claimed feedstuffs are calculated roughly by comparing the potency of the selected compound with that of metiamide in standard pharmacological tests for such activity for example the urethane anesthetized rat test of gastric secretion using histamine as agonist (i.v. metiamide has an $ID_{50}$ of 1.6 $\mu$mol kg$^{-1}$) or the Heidenhain pouch test in dogs using histamine as agonist (orally metiamide has an $ID_{50}$ of 16 $\mu$mol kg$^{-1}$). Details of screening tests are in the International Symposium on Histamine $H_2$-Receptor Antagonists, London, Oct. 1 and 2, 1973, for example, pages 24 and 297. One should recognize however that the optimum dose level for many particular animal species for any specific compound must be determined by feeding trials to determine such a dose level.

One skilled in the veterinary art will recognize that the cost of the chemical ingredient is an important commercial consideration. While certain $H_2$ antagonist compounds other than metiamide may be more active antagonists, the relatively low chemical cost and good efficacy of metiamide makes the use of this compound as active ingredient beneficial.

The active ingredients are used conveniently in the form of their nontoxic salts with acids acceptable in the veterinary or feed supplement fields whenever the base has unfavorable physical characteristics. The formation of the acid addition salts from the basis is documented in the prior art.

As examples of the livestock feed normally ingested per meat producing animal per day are: sheep 3–4 lbs, feed lot steer 20–25 lbs, swine 1–8 lbs, poultry 0.03–1 lb. Thus this invention comprises feeding from 0.03 to 25 lbs per day per animal of a supplemented livestock feed as described above.

Another object of this invention is the method of improving food utilization and growth rate in meat producing animals, which are usually immature growing animals, comprising administering internally to said animals a quantity of a chemical compound having histamine $H_2$ receptor antagonistic activity which quantity is nontoxic and sufficient to increase food utilization and growth rate. The method is conveniently carried out by administering the active ingredient dispersed uniformly throughout the feed of the livestock for oral administration. The animal is either allowed to feed ad libitum or is fed a supplemented feed ration on a planned schedule.

More specifically the quantity of active ingreident used in the method of treating meat producing monogastric and ruminant animals will be chosen from an effective nontoxic amount selected from the range of about 10 mg-2.5 g per day per animal of metiamide base or its biological equivalent of another compound having $H_2$ antagonist activity with consideration of animal weight and relative activity of the antagonist to metiamide. A very useful range is from about 250 mg-750 mg per day of metiamide base equivalents for pigs and cattle.

Generally speaking, for example, a growing meat producing animal such as a young pig, cow (heifer), chicken, turkey or sheep is fed from 0.03-25 lbs. per day of a basal feedstuff containing as active ingredient dispersed therein from about 5-180 grams of compound per ton of feed of a chemical compound having substantial histamine $H_2$ receptor antagonist activity. As noted above, metiamide is the best ingredient known at this time.

Alternatively, but less desirably, the active ingredient may be mixed with the drinking water of the animal. It may also be administered as a sustained release pellet or bolus implanted intramuscularly or subcutaneously in the growing animal. The hind quarters or ear of a pig or heifer are convenient depositories. This means is used if the active ingredient is not orally effective. Methods of using implants are described in U.S. Pat. No. 3,428,729; J. Animal Science 27, 1772 (1968) or J. Biomed. Res. 1 433 (1967). In general several daily doses may be combined in such slow release methods of treatment.

In ruminants one skilled in the art might choose to use one of the many ways available to protect the $H_2$ antagonist active ingredient from the complex biological systems of the rumen to transport the chemical for release to the abomasum and lower digestive tract. For example metiamide is imbedded in or coated by a mixture of glyceryl tristearate and a liquid unsaturated higher fatty acid such as oleic acid. The particulate coated material is then mixed with the feedstuff as described above to be fed to the growing ruminant animal.

The following examples are designed to disclose the best mode of this invention as well as to illustrate the practice of the invention but are not intended to limit the scope of application or the number of active ingredients which can be used in the invention.

EXAMPLE 1

A basal corn based diet is prepared by thoroughly mixing the following ingredients:

| Ingredients | % |
|---|---|
| Ground Corn (to 2 mm size) | 54.62 |
| Soybean Meal (49% protein) | 27.00 |
| Menhaden Fish Meal (60% protein) | 5.00 |
| Meat and Bone Meal | 5.00 |
| Stabilized Animal Fat | 4.00 |
| Dehydrated Alfalfa Meal (17% protein) | 1.25 |
| Dried Whey | 1.00 |
| Limestone | .67 |
| Dicalcium Phosphate Cyphos | .70 |
| Vitamin Premix[a] | .40 |
| Iodized Salt | .23 |
| DL-methionine (98%) | .05 |
| Trace Mineral Mix | .08 |

The corn based ration is mixed with metiamide as follows:

| | Test chemical | Dose in feed (ppm) | Corn basal (grams) | Compound (grams) |
|---|---|---|---|---|
| A | Control | 0 | 100,000 | 0 |
| B | (Metiamide) | 4 | 99,999.6 | 0.4 |
| C | (Metiamide) | 8 | 99,999.2 | 0.8 |
| D | (Metiamide) | 16 | 99,998.4 | 1.6 |

The supplemented ration was fed to 3 day old cockerels with 16 pens each containing 8 chicks used at each dose level. The chicks were allowed to feed at will. The following results were obtained:

| Treatment | ppm | Chick Weight-17 days | % Improvement |
|---|---|---|---|
| Control | 0 | 346.1 | — |
| Metiamide | 4 | 342.0 | −1.2 |
| Metiamide | 8 | 349.2 | +0.9 |
| Metiamide | 16 | 354.4 | +2.4 |

The above data was a configuration of positive results obtained over a dose range earlier in which 4 pens of 8 chicks were used at each dose level with the following results:

| Treatment | ppm | Chick Weight-17 days | % Improvement |
|---|---|---|---|
| Control | 0 | 301.8 | — |
| Metiamide | 8 | 316.9 | +5.0 |
| Metiamide | 40 | 311.5 | +3.2 |
| Metiamide | 200 | 307.3 | +1.8 |

EXAMPLE 2

An example of a suitable premix is as follows:

| Metiamide | 200 g |
|---|---|
| Ground yellow corn | 20 lbs |

EXAMPLE 3

In the field the active ingredients may be administered by means of salt or molasses blocks. A typical block may be prepared using the following conditions:

| Ingredients | Weight percent |
|---|---|
| Dried cane molasses | 39.50 |
| Ground soybean hulls | 29.90 |
| Metiamide | 5.00 |
| Granulated salt | 21.59 |
| Trace minerals and vitamins | 0.20 |
| Stabilized animal fat | 1.11 |
| Moisture | 2.66 |

EXAMPLE 4

| Ingredients | Weight percent |
|---|---|
| Metiamide | 300 mg. |
| Calcium sulfate, dihydrate | 70 mg. |
| Gelatin | 4 mg. |
| Magnesium stearate | 1 mg. |
| Talc | 2 mg. |

The $H_2$-antagonist and calcium sulfate, dihydrate are mixed and passed through a No. 40 standard mesh screen. The screened mixture is then granulated with hot 15 percent gelatin solution, screened through a No. 10 mesh screen and dried overnight at 120° F. The granules are again screened through a No. 40 mesh screen and mixed with the magnesium stearate and talc. The granules are compressed into implants using a ½ inch flat face punch and die. One implant is administered intramuscularly to a feed lot yearling.

EXAMPLE 5

A basal swine feed mixture of standard 16% protein, corn, soy bean meal ration fortified with vitamins and minerals and having dispersed therein metiamide at the concentration of 100 g per ton is fed to 20–25 lb. Hampshire swine.

EXAMPLE 6

| | % by weight |
|---|---|
| Alfalfa hay, leafy ground | 65 |
| Corn shelled | 12 |
| Barley | 9 |
| Soybean meal | 10 |
| Molasses | 2.5 |
| Bone meal | 1 |
| Salt | 0.5 |
| Metiamide | 25 g/ton of feed |

The above mixture is prepared and is fed to feed lot lambs ad libitum.

EXAMPLE 7

Using the same methods and base corn feed as in Example 1 but with 8 pens and 8 chicks at each test level the following data were obtained:

| Chemical | Dose in Feed (ppm) | Weight of Animal | | Feed (grams)/ Gain (grams) | |
|---|---|---|---|---|---|
| | | Day 10 | Day 17 | Day 3–10 | Day 10–17 |
| Control Corn | — | 183.0 g | 359.7 g | 1.97 g/g | 1.84 g/g |
| | | | | Percent of Control | |
| Ranitidine | 8 | 99.9 | 108.1 | 93.0 | 92.1 |
| Tiotidine | 8 | 99.9 | 97.3 | 93.9 | 107.0 |

The other compounds having histamine $H_2$ antagonist activity mentioned above by structure and generic name may be substituted in the foregoing examples for metiamide in quantities from ½ to 1/20 those of metiamide. Other compounds having histamine $H_2$ antagonist activity may be similarly used by comparing their oral and parenteral activity with that of metiamide in standard pharmacological procedures used in the art for demonstrating $H_2$ antagonist activity then adjusting the dosage levels in the particular animal species in question using the methods and compositions of this invention described herein.

What is claimed is:

1. The method of improving food utilization to increase growth rate or feed efficiency in meat producing monogastric and ruminant animals comprising administering orally or parenterally to said animals an effective therefor but not toxic quantity of a chemical compound having histamine $H_2$ receptor antagonist activity.

2. The method of claim 1 in which the animals are chickens or swine.

3. The method of claim 1 in which the animals are growing chickens.

4. The method of claim 1 in which the chemical compound is metiamide.

5. The method of claim 1 in which the chemical compound is metiamide, cimetidine, ranitidine, tiotidine, etintidine or oxmetidine.

6. The method of claim 1 in which the administration is oral and the quantity of said chemical compound is that ingested in the daily diet of a basal feed ration containing from 5–180 grams per ton of feed of said chemical compound.

7. The method of claims 1, 2, 3, 4, 5 or 6 in which the chemical compound is metiamide, the administration is oral dispersed in a livestock feed and the quantity is selected from the range of 6–40 grams per ton of said feed.

8. The method of claims 1, 2, 3, 4, 5 or 6 in which the chemical compound is ranitidine, the administration is oral dispersed in a livestock feed and the quantity is selected from the range of 6–40 grams per ton of said feed.

9. A feed for meat producing animals comprising a quantity of a chemical compound having histamine $H_2$ receptor antagonist activity which is sufficient to improve the food utilization to increase growth rate or feed efficiency of said animals dispersed in a livestock feed ration.

10. The feed of claim 9 in which the chemical compound is metiamide, cimetidine, rantitidine, tiotidine, etintidine or oxmetidine.

11. The feed of claim 9 in which the chemical compound is metiamide.

12. The feed of claim 9 in which the feed is one adapted for poultry and the chemical compound is metiamide.

13. The feed of claim 9 in which the feed is one adapted for swine and the chemical compound is metiamide.

14. The feed of claim 9 in which the chemical compound is ranitidine.

15. The feed of claims 9, 10, 11, 12, 13 or 14 in which the amount of said chemical compound is selected from the range of 5–180 grams per ton of feed.

16. The feed of claim 9 in which the feed is a premix feed comprising a corn based ration combined with 1–3% by weight of the said chemical compound.

17. The feed of claim 9 in which said chemical compound is metiamine or ranitidine which is present in from 6–40 grams per ton of feed.

* * * * *